(12) United States Patent
Kobayashi et al.

(10) Patent No.: US 11,718,579 B2
(45) Date of Patent: Aug. 8, 2023

(54) METHOD FOR PRODUCING HIGHLY POLYMERIZABLE N-VINYL CARBOXYLIC ACID AMIDE MONOMER

(71) Applicant: SHOWA DENKO K.K., Tokyo (JP)

(72) Inventors: Takamitsu Kobayashi, Tokyo (JP); Naoyuki Tanaka, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 50 days.

(21) Appl. No.: 17/595,783

(22) PCT Filed: Dec. 23, 2020

(86) PCT No.: PCT/JP2020/048224
§ 371 (c)(1),
(2) Date: Nov. 24, 2021

(87) PCT Pub. No.: WO2021/132364
PCT Pub. Date: Jul. 1, 2021

(65) Prior Publication Data
US 2022/0227697 A1    Jul. 21, 2022

(30) Foreign Application Priority Data
Dec. 26, 2019    (JP) .................................. 2019-236790

(51) Int. Cl.
*C07C 231/24*    (2006.01)
*C07C 233/05*    (2006.01)

(52) U.S. Cl.
CPC .......... *C07C 231/24* (2013.01); *C07C 233/05* (2013.01)

(58) Field of Classification Search
None
See application file for complete search history.

(56) References Cited

U.S. PATENT DOCUMENTS

| | | |
|---|---|---|
| 3,914,304 A | 10/1975 | Schnabel et al. |
| 5,510,515 A | 4/1996 | Akizawa et al. |
| 5,789,619 A | 8/1998 | Aizawa et al. |
| 5,892,115 A | 4/1999 | Aizawa et al. |
| 6,072,084 A | 6/2000 | Aizawa et al. |
| 6,143,836 A | 11/2000 | Aizawa et al. |
| 6,153,708 A | 11/2000 | Aizawa et al. |
| 7,868,207 B2 | 1/2011 | Okaichi et al. |
| 2009/0270653 A1 | 10/2009 | Okaichi et al. |
| 2009/0287020 A1 | 11/2009 | Uchida et al. |
| 2021/0214302 A1 | 7/2021 | Tanaka |

FOREIGN PATENT DOCUMENTS

| | | |
|---|---|---|
| JP | 50-76015 A | 6/1975 |
| JP | 61-106546 A | 5/1986 |
| JP | 2-188560 A | 7/1990 |
| JP | 7-89916 A | 4/1995 |
| JP | 8-81428 A | 3/1996 |
| JP | 2619204 B2 | 6/1997 |
| JP | 2007-70356 A | 3/2007 |
| JP | 4099831 B2 | 6/2008 |
| JP | 5126764 B2 | 1/2013 |
| WO | 2008/026757 A1 | 3/2008 |
| WO | 2017/145569 A1 | 8/2017 |

OTHER PUBLICATIONS

Machine generated English translation of JPH0789916, obtained Apr. 4, 2023 (Year: 2023).*
Machine generated translation of JP2619204, obtained Apr. 4, 2023 (Year: 2023).*
International Search Report dated Feb. 16, 2021 in International Application No. PCT/JP2020/048224.
Written Opinion of the International Searching Authority dated Feb. 16, 2021 in International Application No. PCT/JP2020/048224.

* cited by examiner

*Primary Examiner* — Amy C Bonaparte
(74) *Attorney, Agent, or Firm* — Sughrue Mion, PLLC

(57) ABSTRACT

A method for producing a highly polymerizable N-vinyl carboxylic acid amide monomer includes (A) melting a crude N-vinyl carboxylic acid amide monomer comprising 50 to 88 mass % of an N-vinyl carboxylic acid amide monomer by heating, followed by cooling for precipitation, and subjecting precipitated N-vinyl carboxylic acid amide monomer crystals to solid-liquid separation (step (A)), and (B) further dissolving the N-vinyl carboxylic acid amide monomer crystals separated in step (A) in a mixed solvent of acetonitrile and an aliphatic hydrocarbon having 6 to 7 carbon atoms, then performing crystallization, performing solid-liquid separation, and recovering an N-vinyl carboxylic acid amide monomer purified product (step (B)), wherein a mass ratio of acetonitrile/N-vinyl carboxylic acid amide monomer crystal in step (B) is 0.01 to 0.5, and a mass ratio of aliphatic hydrocarbon having 6 to 7 carbon atoms/ N-vinyl carboxylic acid amide monomer crystal in step (B) is 0.5 to 3.0.

7 Claims, No Drawings

METHOD FOR PRODUCING HIGHLY POLYMERIZABLE N-VINYL CARBOXYLIC ACID AMIDE MONOMER

CROSS REFERENCE TO RELATED APPLICATIONS

This application is a National Stage of International Application No. PCT/JP2020/048224 filed Dec. 23, 2020, claiming priority based on Japanese Patent Application No. 2019-236790 filed Dec. 26, 2019.

TECHNICAL FIELD

The present invention relates to a method for producing a highly polymerizable N-vinyl carboxylic acid amide monomer. More particularly, the present invention relates to a method for producing an N-vinyl carboxylic acid amide monomer having improved polymerizability, with high productivity.

BACKGROUND ART

An N-vinyl carboxylic acid amide polymer derived from N-vinyl carboxylic acid amide is a water-soluble polymer, and it is dissolved not only in water but also in polar solvents such as alcohols and dimethyl sulfoxide (DMSO). Further, the polymer has characteristics that because of a nonionic polymer, it is not affected by salts or pH, and it has high weathering resistance and high stability particularly to heat. Taking advantage of these characteristics, the polymer is industrially applied to, for example, binders, dispersants, pressure-sensitive adhesives and adhesives, thickening agents, and flocculants.

Regarding a method for producing N-vinyl carboxylic acid amide, many methods have been proposed so far. For example, there is a method in which N-(1-alkoxyethyl) carboxylic acid amide that becomes an intermediate is produced using carboxylic acid amide, acetaldehyde and an alcohol as raw materials and then subjected to thermal cracking or catalytic cracking to synthesize N-vinyl carboxylic acid amide.

In this synthesis reaction for N-vinyl carboxylic acid amide, intermediates such as unreacted N-(1-alkoxyethyl) carboxylic acid amide and carboxylic acid amide are contained other than the N-vinyl carboxylic acid amide. These compounds are similar to the N-vinyl carboxylic acid amide in properties such as boiling point, vapor pressure and solubility, and therefore, it is difficult to purify the N-vinyl carboxylic acid amide by distillation. Then, also regarding a method for purifying N-vinyl carboxylic acid amide, proposals have been made.

In Japanese Patent No. 2619204, a purification method by pressure crystallization is disclosed, and N-vinyl carboxylic acid amide exhibiting high polymerizability is obtained with relatively high purity. This method, however, has a problem as follows; the equipment investment is large, and products cannot be inexpensively provided unless large-scale production is industrially carried out. In Japanese Patent No. 5126764, a solvent crystallization method by an alcohol and an aliphatic hydrocarbon is disclosed. In this combination of the solvents, however, the amount of poor solvent used is large, and the volumetric efficiency is low, so that the productivity is poor.

Moreover, as an N-vinyl carboxylic acid amide polymerization inhibitor, N-1,3-butadienyl carboxylic acid amide is specified in Japanese Patent No. 4099831, and unsaturated aldehyde is specified in International Publication No. WO17/145569, but there are some cases where even if the above substances are removed, good polymerizability is not obtained yet.

CITATION LIST

Patent Literature

Patent Literature 1: Japanese Patent No. 2619204
Patent Literature 2: Japanese Patent No. 5126764
Patent Literature 3: Japanese Patent No. 4099831
Patent Literature 4: International Publication No. WO17/145569

SUMMARY OF INVENTION

Technical Problem

The present invention addresses the problem of providing a method capable of producing a highly polymerizable N-vinyl carboxylic acid amide monomer by efficiently purifying N-vinyl carboxylic acid amide. Moreover, the present invention addresses the problem of producing a high-molecular weight N-vinyl carboxylic acid amide polymer using the N-vinyl carboxylic acid amide monomer produced.

Solution to Problem

The present inventors have earnestly studied a method for producing a highly polymerizable N-vinyl carboxylic acid amide monomer, and as a result, they have found that by combining cooling crystallization with solvent crystallization using acetonitrile and an aliphatic hydrocarbon having 6 to 7 carbon atoms, it becomes possible to produce a highly polymerizable N-vinyl carboxylic acid amide monomer, and they have completed the present invention.

Constitution of the present invention is as follows.

[1] A method for producing a highly polymerizable N-vinyl carboxylic acid amide monomer, comprising (A) a step of melting a crude N-vinyl carboxylic acid amide monomer comprising 50 to 88 mass % of an N-vinyl carboxylic acid amide monomer by heating, followed by cooling for precipitation (cooling crystallization), and subjecting precipitated N-vinyl carboxylic acid amide monomer crystals to solid-liquid separation (step (A)), and (B) a step of further dissolving the N-vinyl carboxylic acid amide monomer crystals separated in the step (A) in a mixed solvent of acetonitrile and an aliphatic hydrocarbon having 6 to 7 carbon atoms, then performing crystallization (solvent crystallization), performing solid-liquid separation, and recovering an N-vinyl carboxylic acid amide monomer purified product (step (B)), wherein a mass ratio of acetonitrile/N-vinyl carboxylic acid amide monomer crystal in the step (B) is 0.01 or more and 0.5 or less, and a mass ratio of aliphatic hydrocarbon having 6 to 7 carbon atoms/N-vinyl carboxylic acid amide monomer crystal in the step (B) is 0.5 or more and 3.0 or less.

[2] The method for producing a highly polymerizable N-vinyl carboxylic acid amide monomer according to [1], wherein the mass of the acetonitrile is 0.003 to 1.0 based on the mass of the aliphatic hydrocarbon having 6 to 7 carbon atoms.

[3] The method for producing a highly polymerizable N-vinyl carboxylic acid amide monomer according to [1] or [2], wherein the crystallization in the step (A) is carried out by melting the crude N-vinyl carboxylic acid amide monomer at 30° C. to 80° C., followed by cooling to −20° C. to 20° C.

[4] The method for producing a highly polymerizable N-vinyl carboxylic acid amide monomer according to any one of [1] to [3], wherein the crystallization in the step (B) is carried out by dissolving the N-vinyl carboxylic acid amide monomer crystals in the mixed solvent of acetonitrile and an aliphatic hydrocarbon having 6 to 7 carbon atoms at 30° C. to 80° C., followed by cooling to −20° C. to 20° C.

[5] The method for producing a highly polymerizable N-vinyl carboxylic acid amide monomer according to any one of [1] to [4], wherein the aliphatic hydrocarbon having 6 to 7 carbon atoms used in the step (B) is at least one selected from normal hexane, cyclohexane, normal heptane, cycloheptane, and methylcyclohexane.

[6] The method for producing a highly polymerizable N-vinyl carboxylic acid amide monomer according to any one of [1] to [5], wherein a method for the solid-liquid separation in the step (A) and the step (B) is separation by filtration.

[7] The method for producing a highly polymerizable N-vinyl carboxylic acid amide monomer according to any one of [1] to [6], wherein the N-vinyl carboxylic acid amide monomer is an N-vinylacetamide monomer.

Advantageous Effect of Invention

According to the present invention, a highly polymerizable N-vinyl carboxylic acid amide monomer that is more excellent in productivity than before can be produced.

DESCRIPTION OF EMBODIMENTS

The method for carrying out the present invention comprises the following steps:

(A) a step of melting a crude N-vinyl carboxylic acid amide monomer comprising 50 to 88 mass % of an N-vinyl carboxylic acid amide monomer by heating, followed by cooling for precipitation (cooling crystallization), and subjecting precipitated N-vinyl carboxylic acid amide monomer crystals to solid-liquid separation (step (A)), and (B) a step of further dissolving the N-vinyl carboxylic acid amide monomer crystals separated in the step (A) in a mixed solvent of acetonitrile and an aliphatic hydrocarbon having 6 to 7 carbon atoms, then performing crystallization (solvent crystallization), performing solid-liquid separation, and recovering an N-vinyl carboxylic acid amide monomer purified product (step (B)).

In the present specification, the "crude N-vinyl carboxylic acid amide monomer" means that it contains not only a component composed of an N-vinyl carboxylic acid amide monomer but also impurities, that is, it is an "unpurified" N-vinyl carboxylic acid amide monomer.

Step (A)

Examples of the N-vinyl carboxylic acid amide monomers include N-vinylformamide, N-vinylacetamide, N-methyl-N-vinylacetamide, N-vinylbenzamide, N-vinyl-N-methylformamide, N-vinyl-N-ethylformamide, N-vinyl-N-ethylacetamide, and N-vinylpyrrolidone. Preferable is N-vinylacetamide.

The crude N-vinylcarboxylic acid amide monomer may be one obtained by any production method. For example, it may be one obtained by synthesizing N-(1-alkoxyethyl) carboxylic acid amide from carboxylic acid amide, acetaldehyde and an alcohol and subjecting this to thermal cracking or catalytic cracking (see Japanese Patent Laid-Open No. 50-76015). Further, it may be one obtained by synthesizing ethylidenebiscarboxylic acid amide from carboxylic acid amide and acetaldehyde and subjecting this to thermal cracking (see Japanese Patent Laid-Open No. 61-106546).

Examples of substances mainly contained in the crude N-vinyl carboxylic acid amide monomer, other than the N-vinyl carboxylic acid amide monomer, include N-(1-alkoxyethyl)carboxylic acid amide, carboxylic acid amide, and alcohols having 1 to 5 carbon atoms, and these are impurities derived from, for example, a method for producing an N-vinyl carboxylic acid amide monomer.

The crude N-vinyl carboxylic acid amide monomer contains an N-vinyl carboxylic acid amide monomer in an amount of 50 to 88 mass %, preferably contains it in an amount of 55 to 85 mass %, and more preferably contains it in an amount of 60 to 85 mass %. When the N-vinyl carboxylic acid amide monomer is contained in an amount of this range, a recovery of the N-vinyl carboxylic acid amide monomer can be increased, and the resulting N-vinyl carboxylic acid amide monomer has high purity and exhibits excellent polymerizability, so that such a range is desirable. When the amount of the N-vinyl carboxylic acid amide monomer contained in the crude N-vinyl carboxylic acid amide monomer is in the range of 50 to 88 mass %, the crude N-vinyl carboxylic acid amide monomer may be used as it is in the production method of the present invention, but the content of the N-vinyl carboxylic acid amide monomer may be appropriately adjusted by operations such as distillation and extraction. By such operations, insoluble components in the crude N-vinyl carboxylic acid amide monomer can be removed in advance.

Usually, the upper limit of the content of the N-vinyl carboxylic acid amide monomer in the crude N-vinyl carboxylic acid amide monomer that is obtained by a known production method is in the above range, but even if a crude N-vinyl carboxylic acid amide monomer in which the content thereof is higher than this upper limit is treated by the production method of the present invention, it is possible to obtain an N-vinyl carboxylic acid amide monomer purified product.

In the step (A), cooling crystallization of the N-vinyl carboxylic acid amide monomer from the crude N-vinyl carboxylic acid amide monomer is carried out. In the cooling crystallization, the crude N-vinyl carboxylic acid amide monomer is melted first. The melting temperature is preferably 30 to 80° C., more preferably 30 to 60° C., and still more preferably 35 to 45° C. When the melting temperature is in the above range, melting of the N-vinyl carboxylic acid amide monomer is easy, and the monomer is not thermally denatured, so that such a melting temperature is desirable.

Next, a solution in which the N-vinyl carboxylic acid amide monomer is dissolved is cooled to precipitate N-vinyl carboxylic acid amide monomer crystals. The cooling temperature is preferably −20° C. to 20° C., more preferably −15 to 15° C., and still more preferably −10° C. to 10° C. When the cooling temperature is in the above range, the cost of equipment such as a refrigerator is small, and the crystallization yield of the N-vinyl carboxylic acid amide monomer is high, so that such a cooling temperature is desirable. Although a temperature difference between the melting temperature and the cooling temperature is not particularly limited, it is preferably 10° C. to 100° C., more preferably 20 to 60° C., and it is appropriately selected according to the treatment efficiency and the filterability of the precipitate.

A method for the efficient solid-liquid separation of the N-vinyl carboxylic acid amide monomer crystals precipitated in the step (A) is preferably separation by filtration. The method for separation by filtration is not limited, and is preferably, for example, centrifugal filtration or pressure filtration from the viewpoints of separation from a crystallization mother liquor and productivity. For improving separability from the mother liquor, it is also preferable to carry out rinsing after the filtration. Solvents used for the rinsing are preferably acetonitrile and an aliphatic hydrocarbon having 6 to 7 carbon atoms, which are the same as the crystallization solvents for use in the step (B). The ratio of the mass of the acetonitrile used in the rinsing to the mass of the crystallization raw material, namely the crude N-vinyl carboxylic acid amide monomer to be treated, is preferably 0.01 to 0.3, more preferably 0.01 to 0.2, and still more preferably 0.02 to 0.1. The ratio of the mass of the aliphatic hydrocarbon having 6 to 7 carbon atoms used in the rinsing to the mass of the crude N-vinyl carboxylic acid amide monomer used is preferably 0.1 to 3.0, more preferably 0.1 to 2.0, and still more preferably 0.1 to 1.0.

The mass of the acetonitrile used is preferably 0.001 to 3.0, more preferably 0.005 to 2.0, and still more preferably 0.01 to 0.5, based on the mass of the aliphatic hydrocarbon having 6 to 7 carbon atoms used.

Step (B)

In the step (B), the recovered N-vinyl carboxylic acid amide monomer crystals are dissolved in acetonitrile that is a crystallization solvent in the presence of an aliphatic hydrocarbon having 6 to 7 carbon atoms that is a poor solvent, and thereafter, crystallization is carried out. Such a crystallization method is referred to as solvent crystallization. The recovered N-vinyl carboxylic acid amide monomer crystals contain an N-vinyl carboxylic acid amide monomer in an amount of 88 mass % or more, preferably contain it in an amount of 90 mass % or more, and more preferably contain it in an amount of 92 mass % or more. The N-vinyl carboxylic acid amide monomer crystals sometimes contain the aforesaid crystallization mother liquor and the mother liquor used for rinsing, other than the N-vinyl carboxylic acid amide monomer.

The ratio of the mass of the acetonitrile used to the mass of the N-vinyl carboxylic acid amide monomer crystals used is 0.01 or more and 0.5 or less, preferably 0.02 to 0.4, and more preferably 0.03 to 0.3.

As the aliphatic hydrocarbons having 6 to 7 carbon atoms used, normal hexane, cyclohexane, methylcyclohexane, normal heptane and cycloheptane are preferable, and cyclohexane and methylcyclohexane are more preferable. Aliphatic hydrocarbons having 5 or less carbon atoms are difficult to handle because of low boiling points, and aliphatic hydrocarbons having 8 or more carbon atoms have high boiling points and cannot be removed from the crystals sometimes. The ratio of the mass of the aliphatic hydrocarbon having 6 to 7 carbon atoms to the mass of the N-vinyl carboxylic acid amide monomer crystals used is 0.5 or more and 3.0 or less, and preferably 0.5 to 2.0. When the ratio is in this range, a recrystallized substance of the N-vinyl carboxylic acid amide monomer is sufficiently precipitated, and moreover, the amount of solvent used is not large and the volumetric efficiency of a crystallization apparatus can be increased, so that such a ratio is desirable.

The mass of the acetonitrile used is preferably 0.003 to 1.0, more preferably 0.005 to 0.8, and still more preferably 0.01 to 0.5, based on the mass of the aliphatic hydrocarbon having 6 to 7 carbon atoms used.

The temperature to dissolve the N-vinyl carboxylic acid amide monomer crystals is preferably 30 to 80° C., more preferably 30 to 60° C., and still more preferably 35 to 45° C. This temperature range is desirable because the N-vinyl carboxylic acid amide is not denatured and is sufficiently dissolved.

Subsequently, the dissolved N-vinyl carboxylic acid amide monomer is cooled to precipitate a recrystallized substance. This cooling temperature is preferably −20° C. to 20° C., more preferably −15 to 15° C., and still more preferably −10° C. to 10° C. This temperature range is desirable because the cost of equipment is small, and the crystallization yield is sufficient.

The recrystallized substance of the N-vinyl carboxylic acid amide monomer is recovered, and an N-vinyl carboxylic acid amide monomer purified product is produced.

A method for efficiently separating the N-vinyl carboxylic acid amide monomer recrystallized substance precipitated in the step (B) is preferably separation by filtration. The method for separation by filtration is not limited, and is preferably, for example, centrifugal filtration or pressure filtration from the viewpoints of separation from a crystallization mother liquor and productivity. For improving separability from the mother liquor, it is also preferable to carry out rinsing after the filtration. Solvents used for the rinsing are preferably acetonitrile and an aliphatic hydrocarbon having 6 to 7 carbon atoms, which are the same as the crystallization solvents. The ratio of the mass of the acetonitrile used in the rinsing to the mass of the N-vinyl carboxylic acid amide monomer crystals recovered from the step (A) is preferably 0.01 to 0.3, more preferably 0.01 to 0.2, and still more preferably 0.02 to 0.1. The ratio of the mass of the aliphatic hydrocarbon having 6 to 7 carbon atoms used in the rinsing to the mass of the N-vinyl carboxylic acid amide monomer crystals recovered from the step (A) is preferably 0.1 to 3.0, more preferably 0.1 to 2.0, and still more preferably 0.1 to 1.5.

In order to make the purity of the resulting N-vinyl carboxylic acid amide monomer purified product higher, the steps (A) and (B) may be repeated.

The highly polymerizable N-vinyl carboxylic acid amide monomer produced as above has high purity and high polymerizability.

In the mother liquor recovered in the steps (A) and (B), synthetic raw materials for the N-vinyl carboxylic acid amide monomer, such as an alcohol, carboxylic acid amide, and N-(1-alkoxyethyl)carboxylic acid amide, are contained. These may be returned to the production process for the crude N-vinyl carboxylic acid amide monomer, such as a synthesis process for N-(1-alkoxyethyl)carboxylic acid amide, and reused.

The highly polymerizable N-vinyl carboxylic acid amide monomer produced as above can be properly polymerized and used. For example, it can be utilized as a homopolymer obtained by polymerizing monomers containing the high purity N-vinyl carboxylic acid amide monomer obtained by the above production method, or a copolymer obtained by polymerizing the N-vinyl carboxylic acid amide monomer and other monomers. These (co)polymers are water-soluble and are used in various applications.

Examples of the other monomers include (meth)acrylic acid-based monomers, such as (meth)acrylic acid or its salt, methyl (meth)acrylate, ethyl (meth)acrylate, (iso)propyl (meth)acrylate, butyl (meth)acrylate, octyl (meth)acrylate, 2-ethylhexyl (meth)acrylate, methoxyethyl (meth)acrylate, 2-hydroxyethyl (meth)acrylate, 2-hydroxypropyl (meth)acrylate, and polyoxyalkylene glycol mono(meth)acrylate; (meth)acrylamide-based monomers, such as (meth)acrylamide, N,N-dimethyl(meth)acrylamide, N,N-diethyl(meth)acrylamide, N-methylol (meth)acrylamide, 2-(meth)acrylamido-2-methylpropanesulfonic acid or its salt, and N-isopropyl(meth)acrylamide; vinyl ester-based monomers, such as vinyl acetate, vinyl butyrate, and vinyl valerate; styrene-based monomers, such as styrene, α-methylstyrene, p-methylstyrene, p-methoxystyrene, and m-chlorostyrene; vinyl ether-based monomers, such as methyl vinyl ether, butyl vinyl ether, and vinyl benzyl ether; dicarboxylic acid-based monomers, such as maleic anhydride, maleic acid or its salt, fumaric acid or its salt, maleic acid dimethyl ester, and fumaric acid diethyl ester; allyl monomers, such as allyl alcohol, allyl phenyl ether, and allyl acetate; and monomers, such as (meth)acrylonitrile, vinyl chloride, ethylene, and propylene.

The above other monomers may be used singly or may be used in combination of two or more. The amounts of the above other monomers may be appropriately determined according to the use application of the copolymer, but it is desirable to usually use them in amounts of 60 mass % or less, preferably 40 mass % or less, in the total of the monomers.

When the highly polymerizable N-vinyl carboxylic acid amide monomer of the present invention is polymerized, a polymerization initiator may be used. As the polymerization initiators, those generally used for radical polymerization of vinyl compounds can be used without any limitation. Examples thereof include redox type polymerization initiators, azo compound type polymerization initiators, and peroxide type polymerization initiators.

These may be used singly or may be used in combination of two or more.

The above (co)polymer is suitably used in a wide range of fields utilizing its functions such as thickening effect and dispersing effect. Specific examples are given below, but are not limited thereto.

(1) Dispersant for Industrial Use

The (co)polymer is used as a dispersant for, for example, inorganic and organic various powders. More specifically, regarding inorganic powders, such as silica, alumina, titania, and calcium carbonate; mineral-based powders, such as talc and kaolin; various pigment powders, such as carbon black; resin powders, such as polyurethane, polyacrylic acid ester, and polyethylene; and organic powders, such as stearic acid salt, the (co)polymer is used as a dispersant in various polar solvents such as water.

(2) Thickening Agent and Dispersant Used for, for Example, Coating Material and Ink Regarding, for example, coating materials and inks, the (co)polymer is used as an additive dispersant; a modifier for viscosity or leveling; or a wettability improver.

(3) Treatment Agent and Collecting Agent Used for Water and Oil (4) Cosmetics

Regarding cosmetics, such as shampoo, hair conditioner and lotion, the (co)polymer is used for an emulsion stabilizer, a lubricant, an emulsion type cosmetic (used as an emulsifier), a film type pack agent, and a hair setting agent.

(5) Toiletry Product

The (co)polymer is used as a thickening agent for, for example, liquid detergents (for clothes, for kitchen, for bathroom and tiles), toothpastes, cleansers, softeners, and detergents for industrial use.

(6) Pressure-Sensitive Adhesive and Its Aid (7) Medical Field

For example, tablets (sustained release drugs), enteric drugs, base materials for patches such as poultices and plasters, external ointments, drug release control preparations, gastric suspended sustained release preparations, mucosal administration preparations, the composition for outer skin (medical film), wound covering protective material, dental material, oral absorbent, interdental cleaning tool, etc., the (co)polymer is used for retention and sustained release of the drug. Furthermore, the (co)polymer is used as a lubricant for medical devices such as urethral catheters and enemas that are heated in an autoclave for disinfection and repeatedly used, and as a viscosity modifier for diagnostic agents.

(8) Water Absorbing Material, Water Retention Agent, Sealing Agent, Refrigerant (9) Others The (co)polymer is used for, for example, treatment agents for papermaking; deodorants; desiccants; fermentation aids; release agents for packing materials and old walls, and moreover, it is used as a thickening agent for, for example, electrolyte supports of toys, accessories for soaking up sweat, contact media for ultrasonic flow detection, ultrasonic probes, and batteries and sensors.

EXAMPLES

The present invention will be more specifically described with reference to examples, but the present invention is in no way limited to these examples.

An analytical method for a highly polymerizable N-vinylacetamide monomer obtained by the production method of the present invention is shown below. The analytical method is not limited to the following one, and a known method can be adopted.

Compositional Analysis

Purities of N-vinylacetamide monomers obtained in the examples and the comparative examples are determined by GC analysis under the following conditions.

Apparatus: high-performance general-purpose gas chromatograph "GC-2014" (manufactured by Shimadzu Corporation)
Column: DB-WAX (0.25 mm×30 m, manufactured by Agilent Technologies, Inc.)
Type of carrier gas: He
Flow rate of carrier gas: 1 mL/min
Split ratio: 40
Column temperature: Heating program was set in order of 40° C. (7 min)→heating (25° C./min)→130° C. (15 min)→heating (30° C./min)→220° C. (7 min).
Injection temperature: 200° C.
Detector: hydrogen flame ionization detector (FID)
Detector temperature: 230° C.

The N-vinyl acetamide monomer was confirmed and identified from an ultraviolet-visible spectroscopic absorption spectrum through high-performance liquid column chromatography (HPLC). The measurement conditions are as follows.

Column: manufactured by SHOWA DENKO K.K.: Shodex® SIL-5B
Eluent: isopropyl alcohol (IPA)/N-hexane=1/9 (mass ratio)
Column temperature: 40° C.
Flow rate: 1.0 mL/min
Detector: ultraviolet-visible spectroscopic detector, 254 nm Polymerizability Test Polymerizability of the resulting N-vinyl acetamide monomer purified product is evaluated by the polymerizability test shown below.

[1] A 100 ml glass container equipped with a catalyst injection tube, a nitrogen gas blowpipe, a nitrogen gas exhaust pipe and a thermometer is prepared.

[2] Into the glass container of [1], 20 g of an N-vinyl acetamide monomer purified product and 58 g of ion-exchanged water are weighed.

[3] While bubbling nitrogen gas at 50 cm³/min, the glass container is heated to 30° C. in a water bath. Nitrogen gas is passed through until polymerization is completed.

[4] To 1.6 g of 2,2'-azobis[2-(2-imidazolin-2-yl)propane] dihydrochloride (V-044 manufactured by FUJIFILM Wako Pure Chemical Corporation) as a polymerization initiator, 48.4 g of ion-exchanged water is added to dissolve it.

[5] To 4.0 g of 2,2'-azobis(2-methylpropionamidine) dihydrochloride (V-50 manufactured by FUJIFILM Wako Pure Chemical Corporation) as a polymerization initiator, 46.0 g of ion-exchanged water is added to dissolve it.

[6] When one hour of passing of nitrogen gas has elapsed, 1.0 g of the polymerization initiator solution of [4] and 1.0 g of the polymerization initiator solution of [5] are successively added by a syringe.

[7] The glass container is taken out of the water bath, water on the glass surface is removed with paper, and then the glass container is transferred into an insulating container to continue polymerization.

[8] The polymerization temperature is monitored, and a standard temperature peak arrival time from the addition of the polymerization initiators in [6] (time from the polymerization initiator injection to the temperature peak arrival) is taken as an index of polymerizability. A judgement whether the polymerizability is good or bad is made based on the standard temperature peak arrival time, and a time of less than 120 minutes is judged to be good.

Synthesis Example 1

In the presence of a sulfuric acid catalyst, 224 g of acetaldehyde, 325 g of methanol and 100 g of acetamide were allowed to react at 40° C. to synthesize N-(1-methoxyethyl)acetamide having pH 1.2. To the reaction solution, a 48 mass % sodium hydroxide aqueous solution was added to adjust the pH to 8.3. Thereafter, low-boiling components were distilled off by a simple distillation apparatus at a temperature of 60 to 70° C. and a pressure of 33 kPa (absolute pressure), and then, water and methanol were distilled off at a temperature of 70° C. and a pressure of 0.3 kPa (absolute pressure), thereby obtaining 151 g of N-(1-methoxyethyl)acetamide having a purity of 92 mass %.

Subsequently, the N-(1-methoxyethyl)acetamide was fed to a reactor (tube type reactor having inner diameter of 20 mm and length of 240 mm) having been kept at 400° C. and 20 kPa (absolute pressure), at a rate of 1.5 g/min. In a cooling tube installed at the reactor exit, a mixture of N-vinylacetamide produced by thermal cracking reaction and methanol was condensed, thereby obtaining a crude N-vinylacetamide recovered substance. The conversion ratio of the N-(1-methoxyethyl)acetamide was 90%.

Subsequently, the column was packed with a 0.3% Pd—$Al_2C_3$ catalyst (the packing amount was such an amount that the catalytic amount became 1 ml based on 20 g of the crude N-vinylacetamide recovered substance), then the crude N-vinylacetamide recovered substance was circularly passed through at a reaction temperature of 40° C. and a hydrogen gas pressure of 0.03 MPa (gauge pressure) in such a manner that the space velocity (SV value) in the catalyst-packed column became 100/hour, and N-1,3-butadienylacetamide produced as a by-product by the thermal cracking reaction was hydrogenated and thereby decreased in quantity.

The reaction was carried out until the amount of the N-1,3-butadienylacetamide became 30 mass ppm or less. The crude N-vinylacetamide recovered substance in which the amount of the N-1,3-butedienylacetamide had been decreased was distilled using a simple distillation apparatus under the conditions of a vacuum degree of 0.3 kPa (absolute pressure) or less and a bottom temperature of 60° C. or less to remove methanol, thereby obtaining 120 g of a crude N-vinylacetamide monomer. The purity of the N-vinylacetamide monomer in this crude N-vinylacetamide monomer was 75 mass %.

Example 1

The crude N-vinylacetamide monomer obtained in Synthesis Example 1 was heated to 40° C. and thereby melted in a crystallization apparatus, then subjected to cooling crystallization from 40° C. down to 10° C. over a period of 6 hours, transferred into a centrifugal filter, subjected to solid-liquid separation using the centrifugal filter, and thereafter rinsed with acetonitrile 4 g/methylcyclohexane 77 g, thereby obtaining 52 g of crystals of an N-vinylacetamide monomer. The purity of the N-vinylacetamide at this time was 95 mass %.

To 52 g of these N-vinylacetamide monomer crystals, 2.6 g of acetonitrile and 57 g of methylcyclohexane were added, and they were heated to 40° C. to dissolve the crystals and thereafter cooled to 5° C. over a period of 7 hours to perform solvent crystallization, thereby precipitating a recrystallized substance of the N-vinylacetamide monomer. Thereafter, a slurry containing the recrystallized substance was transferred into a centrifugal filter, subjected to solid-liquid separation using the centrifugal filter and thereafter rinsed with acetonitrile 1 g/methylcyclohexane 25 g, and then, the recrystallized substance was recovered to obtain a purified product of an N-vinylacetamide monomer. The amount of the resulting purified product was 45 g, and the purity of the N-vinylacetamide monomer was 99.8 mass %.

The resulting N-vinylacetamide monomer purified product was subjected to a polymerizability test. The test result was 104 minutes.

Example 2

A recrystallized substance of an N-vinylacetamide monomer was precipitated in the same manner as in Example 1, except that in the solvent crystallization, the amounts of the acetonitrile and the methylcyclohexane used were changed to 10 g and 57 g, respectively. Thereafter, a slurry containing the recrystallized substance was sent to a centrifugal filter, subjected to solid-liquid separation, and rinsed, and then, the recrystallized substance was recovered to obtain a purified product of the N-vinylacetamide monomer. The amount of the resulting purified product was 33 g, and the purity thereof was 99.8 mass %. The result of the polymerizability test was 98 minutes.

Example 3

A recrystallized substance of an N-vinylacetamide monomer was precipitated in the same manner as in Example 1, except that in the solvent crystallization and rinsing, normal hexane was used instead of the methylcyclohexane. Thereafter, a slurry containing the recrystallized substance was sent to a centrifugal filter, subjected to solid-liquid separation, and rinsed, and then, the recrystallized substance was recovered to obtain a purified product of the N-vinylacetamide monomer. The amount of the resulting purified product was 44 g, and the purity thereof was 99.8 mass %. The result of the polymerizability test was 110 minutes.

Example 4

A recrystallized substance of an N-vinylacetamide monomer was precipitated in the same manner as in Example 1, except that in the solvent crystallization and rinsing, cyclohexane was used instead of the methylcyclohexane. Thereafter, a slurry containing the recrystallized substance was sent to a centrifugal filter, subjected to solid-liquid separation using the centrifugal filter, and rinsed, and then, the recrystallized substance was recovered to obtain a purified product of the N-vinylacetamide monomer. The amount of the resulting purified product was 43 g, and the purity thereof was 99.7 mass %. The result of the polymerizability test was 98 minutes.

Comparative Example 1

In Example 1, only the cooling crystallization was carried out without carrying out the solvent crystallization. The amount of the resulting crystals of the N-vinylacetamide monomer was 52 g, and the purity thereof was 95 mass %. The resulting N-vinylacetamide monomer crystals were subjected to a polymerizability test, and the test results were 160 minutes and bad polymerizability.

Comparative Example 2

To 100 g of a crude N-vinylacetamide monomer which had been obtained in the same manner as in Synthesis Example 1 and from which methanol had been removed, 5 g of acetonitrile and 110 g of methylcyclohexane were added without carrying out cooling crystallization, they were heated to 40° C. to dissolve the monomer and then cooled to 5° C. over a period of 7 hours to perform solvent crystallization, and further, cooling to 0° C. was carried out over a period of one hour, but precipitation of crystals was not observed, and an N-vinylacetamide monomer was not able to be obtained.

Comparative Example 3

A recrystallized substance of an N-vinylacetamide monomer was precipitated in the same manner as in Example 1, except that in the solvent crystallization, 20 g of acetonitrile was used, and methylcyclohexane was not used. The amount of solvent was small, and fluidity of the slurry was considerably deteriorated, but the recrystallized substance of the N-vinylacetamide monomer was transferred into a centrifugal filter, subjected to solid-liquid separation using the centrifugal filter, and thereafter rinsed with acetonitrile 1 g/methylcyclohexane 25 g, and then, the recrystallized substance was recovered. The amount of the resulting purified product was 21 g, and the purity thereof was 99.7 mass %. The result of the polymerization test was 112 minutes.

Comparative Example 4

In the solvent crystallization, 31 g of acetonitrile and 208 g of methylcyclohexane were used, so that the capacity of the crystallization apparatus needed to be increased, and the volumetric efficiency significantly decreased to ¼. A recrystallized substance of an N-vinylacetamide monomer was precipitated in the same manner as in Example 1, except for this. Since the amount of solvent used was large, a precipitate liquid containing the recrystallized substance of the N-vinylacetamide monomer was divided and introduced into a centrifugal filter, subjected to solid-liquid separation using the centrifugal filter, and thereafter rinsed with acetonitrile 1 g/methylcyclohexane 25 g, and then the recrystallized substance was recovered. The amount of the resulting purified product was 7 g, and the purity thereof was 99.8 mass %. The amount recovered was small, and the polymerizability test was not able to be carried out.

The crystallization conditions and the evaluation results are set forth together in Table 1.

TABLE 1

| | Solvent crystallization | | | | |
|---|---|---|---|---|---|
| | | Mass ratio (wt/wt-NVA) | | NVA | Evaluation Polymeriza- |
| | Cooling crystallization | ATN | Poor solvent | yield (%) | bility test (min, ≤120 min) |
| Example 1 | Performed | 0.05 | 1.1 | 91 | 104 |
| Example 2 | Performed | 0.2 | 1.1 | 67 | 98 |
| Example 3 | Performed | 0.05 | 1.1 *1 | 89 | 110 |
| Example 4 | Performed | 0.05 | 1.1 *2 | 87 | 98 |
| Comparative Example 1 | Performed | Not performed | | — | 160 |
| Comparative Example 2 | Not performed | 0.05 | 1.1 | 0 | — |
| Comparative Example 3 | Performed | 0.4 | 0 | 42 | 112 |
| Comparative Example 4 | Performed | 0.6 | 4 | 14 | — |

*1 normal hexane,
*2 cyclohexane, in other examples and the comparative examples, methylcyclohexane
NVA: N-vinylacetamide monomer,
ATN: acetonitrile

INDUSTRIAL APPLICABILITY

The N-vinyl carboxylic acid amide monomer obtained by the present invention is utilized for producing an N-vinyl carboxylic acid amide polymer that is utilized for, for example, a flocculant, a thickening agent, a dispersant, and a pressure-sensitive adhesive.

The invention claimed is:
1. A method for producing a highly polymerizable N-vinyl carboxylic acid amide monomer, comprising
   (A) a step of melting a crude N-vinyl carboxylic acid amide monomer comprising 50 to 88 mass % of an N-vinyl carboxylic acid amide monomer by heating, followed by cooling for precipitation, and subjecting precipitated N-vinyl carboxylic acid amide monomer crystals to solid-liquid separation, and
   (B) a step of further dissolving the N-vinyl carboxylic acid amide monomer crystals separated in the step (A) in a mixed solvent of acetonitrile and an aliphatic hydrocarbon having 6 to 7 carbon atoms, then performing crystallization, performing solid-liquid separation, and recovering an N-vinyl carboxylic acid amide monomer purified product, wherein
   a mass ratio of acetonitrile/N-vinyl carboxylic acid amide monomer crystal in the step (B) is 0.01:1.0 or more and 0.5:1.0 or less, and
   a mass ratio of aliphatic hydrocarbon having 6 to 7 carbon atoms/N-vinyl carboxylic acid amide monomer crystal in the step (B) is 0.5:1.0 or more and 3.0:1.0 or less.

2. The method for producing a highly polymerizable N-vinyl carboxylic acid amide monomer according to claim 1, wherein the mass of the acetonitrile is 0.003:1.0 to 1.0:1.0 based on the mass of the aliphatic hydrocarbon having 6 to 7 carbon atoms.

3. The method for producing a highly polymerizable N-vinyl carboxylic acid amide monomer according to claim 1, wherein the crystallization in the step (A) is carried out by melting the crude N-vinyl carboxylic acid amide monomer at 30° C. to 80° C., followed by cooling to −20° C. to 20° C.

4. The method for producing a highly polymerizable N-vinyl carboxylic acid amide monomer according to claim 1, wherein the crystallization in the step (B) is carried out by dissolving the N-vinyl carboxylic acid amide monomer crystals in the mixed solvent of acetonitrile and an aliphatic hydrocarbon having 6 to 7 carbon atoms at 30° C. to 80° C., followed by cooling to −20° C. to 20° C.

5. The method for producing a highly polymerizable N-vinyl carboxylic acid amide monomer according to claim 1, wherein the aliphatic hydrocarbon having 6 to 7 carbon atoms used in the step (B) is at least one selected from normal hexane, cyclohexane, normal heptane, cycloheptane, and methylcyclohexane.

6. The method for producing a highly polymerizable N-vinyl carboxylic acid amide monomer according to claim 1, wherein the method for the solid-liquid separation in the step (A) and the step (B) is separation by filtration.

7. The method for producing a highly polymerizable N-vinyl carboxylic acid amide monomer according to claim 1, wherein the N-vinyl carboxylic acid amide monomer is an N-vinylacetamide monomer.

* * * * *